(12) United States Patent
Sato et al.

(10) Patent No.: US 11,087,406 B2
(45) Date of Patent: Aug. 10, 2021

(54) RISK ANALYSIS SYSTEM AND RISK ANALYSIS METHOD

(71) Applicants: OMRON HEALTHCARE CO., LTD., Muko (JP); OMRON Corporation, Kyoto (JP)

(72) Inventors: Hironori Sato, Kyoto (JP); Mitsuharu Konishi, Kyoto (JP); Seisuke Fujiwara, Kyoto (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 0 days.

(21) Appl. No.: 16/237,802

(22) Filed: Jan. 2, 2019

(65) Prior Publication Data

US 2019/0139146 A1 May 9, 2019

Related U.S. Application Data

(63) Continuation of application No. PCT/JP2017/023511, filed on Jun. 27, 2017.

(30) Foreign Application Priority Data

Jul. 6, 2016 (JP) .............................. JP2016-134248

(51) Int. Cl.
*G06Q 10/10* (2012.01)
*H04W 4/029* (2018.01)
(Continued)

(52) U.S. Cl.
CPC ............. *G06Q 40/08* (2013.01); *A61B 5/021* (2013.01); *G06Q 10/0635* (2013.01); *G16H 50/30* (2018.01); *G06Q 50/22* (2013.01)

(58) Field of Classification Search
CPC ........................... G06Q 40/08; G06Q 10/0635
(Continued)

(56) References Cited

U.S. PATENT DOCUMENTS

| 7,249,040 | B1 | 7/2007 | Binns et al. | |
| 2005/0182659 | A1* | 8/2005 | Huttin | G06Q 10/06 705/2 |

(Continued)

FOREIGN PATENT DOCUMENTS

| JP | 2003-031127 A | 1/2003 |
| JP | 2004-078479 A | 3/2004 |

(Continued)

OTHER PUBLICATIONS

Official Communication issued in International Patent Application No. PCT/JP2017/023511, dated Sep. 5, 2017.

(Continued)

*Primary Examiner* — Hai Tran
(74) *Attorney, Agent, or Firm* — Keating and Bennett, LLP

(57) ABSTRACT

The risk analysis system according to the present invention includes: a storage apparatus which stores subject data including information related to health of a subject; an analyzer which analyzes a risk related to the health of the subject based on the subject data acquired from the storage apparatus; and an output apparatus which outputs an analysis result by the analyzer. The analyzer has: a risk estimating unit which estimates an event onset risk of the subject based on the subject data; and a medical expense predicting unit which predicts future medical expenses, which are medical expenses to be incurred in the future by the subject, based on the event onset risk estimated by the risk estimating unit and the subject data.

19 Claims, 8 Drawing Sheets

(51) Int. Cl.
   *G01C 21/26* (2006.01)
   *G06Q 40/08* (2012.01)
   *G06Q 10/06* (2012.01)
   *G16H 50/30* (2018.01)
   *A61B 5/021* (2006.01)
   *G06Q 50/22* (2018.01)

(58) Field of Classification Search
   USPC .............................................................. 705/4
   See application file for complete search history.

(56) References Cited

U.S. PATENT DOCUMENTS

| | | | |
|---|---|---|---|
| 2005/0234742 A1 | 10/2005 | Hodgdon | |
| 2007/0112593 A1 | 5/2007 | Daya | |
| 2008/0183454 A1* | 7/2008 | Barabasi | G16H 50/70 703/11 |
| 2010/0280395 A1 | 11/2010 | Lin | |
| 2011/0166978 A1* | 7/2011 | Mastrogiovanni | G06Q 40/06 705/35 |
| 2011/0202486 A1 | 8/2011 | Fung et al. | |
| 2011/0313790 A1 | 12/2011 | Yao | |
| 2014/0025395 A1 | 1/2014 | Averill et al. | |
| 2014/0052008 A1 | 2/2014 | Kim et al. | |
| 2014/0073882 A1 | 3/2014 | Choi et al. | |
| 2014/0316290 A1* | 10/2014 | Kobayashi | A61B 5/02141 600/490 |
| 2014/0343966 A1 | 11/2014 | Miyoshi et al. | |

FOREIGN PATENT DOCUMENTS

| | | |
|---|---|---|
| JP | 2005-050210 A | 2/2005 |
| JP | 2005-052164 A | 3/2005 |
| JP | 2007-523410 A | 8/2007 |
| JP | 2010-026855 A | 2/2010 |
| JP | 2011-039653 A | 2/2011 |
| JP | 2011-070405 A | 4/2011 |
| JP | 2014-225175 A | 12/2014 |
| JP | 2016-004430 A | 1/2016 |
| WO | 2016/040253 A1 | 3/2016 |

OTHER PUBLICATIONS

Official Communication issued in corresponding Japanese Patent Application No. 2018-001807, dated Jul. 14, 2020.
Official Communication issued in corresponding Japanese Patent Application No. 2018-001838, dated Jul. 14, 2020.
"Guidelines for the Management of Hypertension 2014", Japan Hypertension Research Institute, Oct. 21, 2015, 6 pages.
Official Communication issued in corresponding Singaporean Patent Application No. 11201811793P, dated Dec. 4, 2020.
Official Communication issued in corresponding Singaporean Patent Application No. 11201811793P, dated Dec. 7, 2020.

* cited by examiner

DISPLAY EXAMPLE TO INSURANCE SUBSCRIPTION APPLICANT

```
THIS HEALTH INSURANCE IS SUITABLE FOR YOU.

INSURANCE POLICY:   XX HEALTH INSURANCE   PLAN A
TOTAL AMOUNT OF INSURANCE PREMIUM OVER 10 YEARS:  3,500,000 YEN
PREDICTED MEDICAL EXPENSES OVER 10 YEARS:         5,300,000 YEN
```

*FIG.5A*

DISPLAY EXAMPLE TO INSURER

```
PROPRIETY OF UNDERWRITING OF MR. A: INAPPROPRIATE

INSURANCE POLICY:   XX HEALTH INSURANCE   PLAN A
TOTAL AMOUNT OF INSURANCE PREMIUM OVER 10 YEARS:  3,500,000 YEN
PREDICTED MEDICAL EXPENSES OVER 10 YEARS:         5,300,000 YEN
```

*FIG.5B*

EXAMPLE OF RECOMMENDATION TO
INSURANCE SUBSCRIPTION APPLICANT OR INSURER

```
HEALTH INSURANCE SUITABLE FOR MR. A IS

XX HEALTH INSURANCE   PLAN A.

(INSURANCE PREMIUM AMOUNT: xxxxxx YEN)
```

*FIG.5C*

| USER ID | AGE | GENDER | BP TREND (AVE/MAX/MIN) | OFFICE BP | HOME BP | VASCULAR AGE | TOTAL RISK |
|---|---|---|---|---|---|---|---|
| 31499 | 75 | FEMALE | (143/168/135) | 164 | 143 | 70 | High |
| 31965 | 75 | FEMALE | (112/130/110) | 145 | 112 | 54 | Middle |
| 34408 | 58 | MALE | (180/195/162) | 140 | 180 | 89 | Very High |
| 35890 | 68 | MALE | (113/135/105) | 144 | 113 | 54 | Low |
| ... | ... | ... | ... | ... | ... | ... | ... |

FIG.6

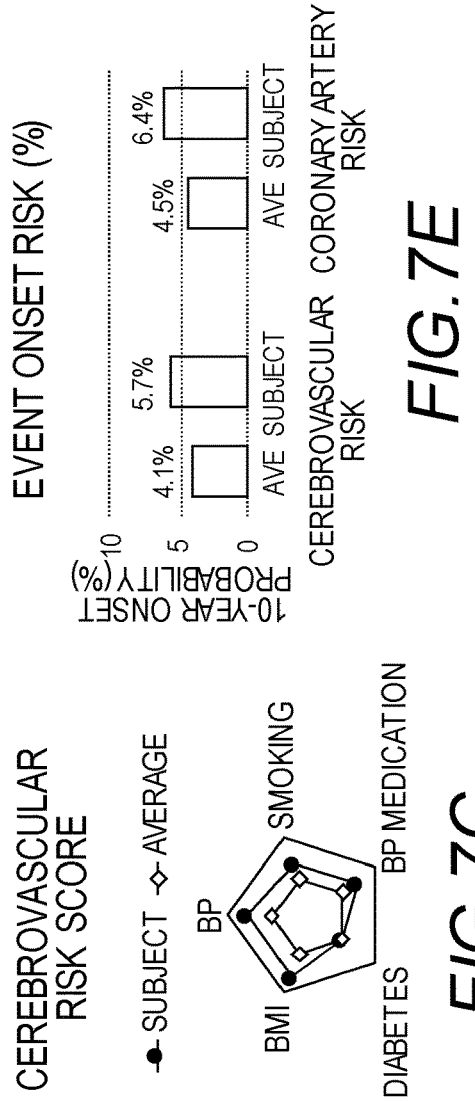
FIG.7A
FIG.7B
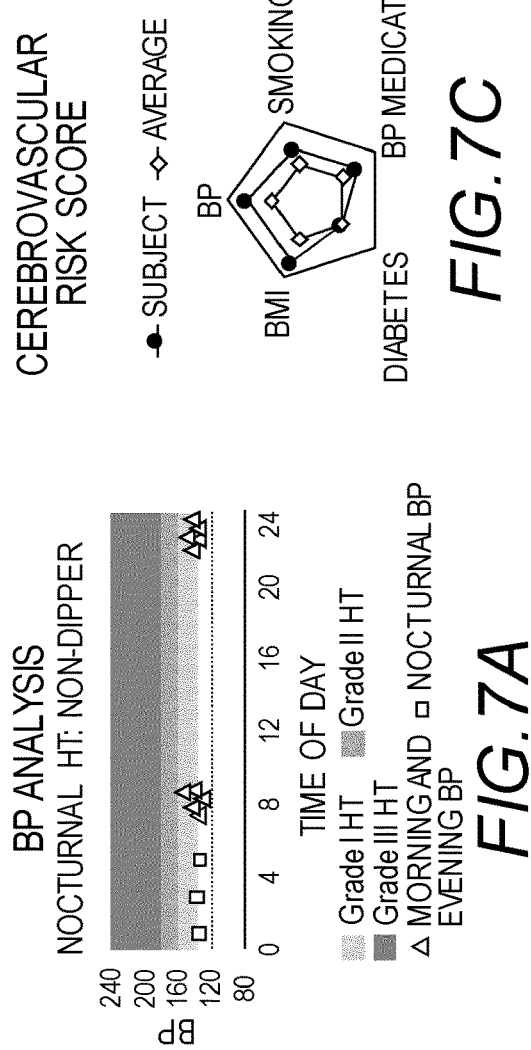
FIG.7C
FIG.7E
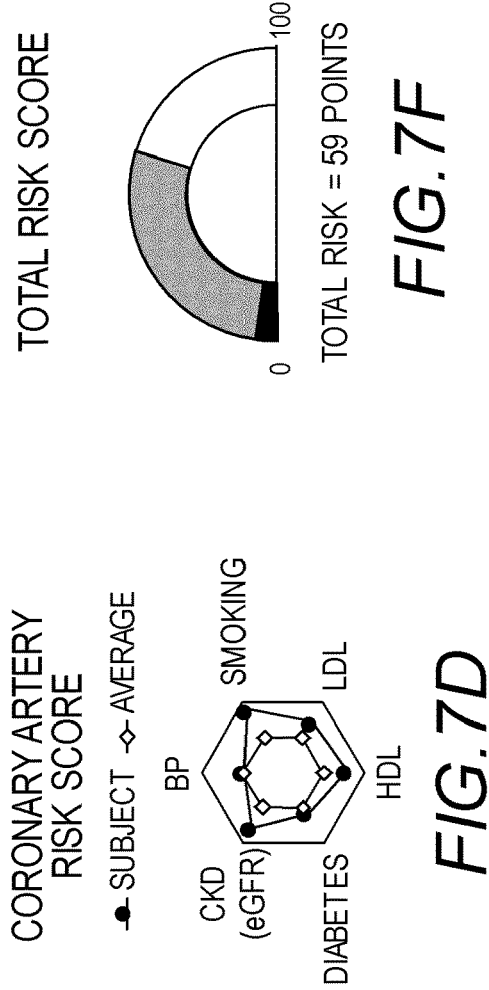
FIG.7D
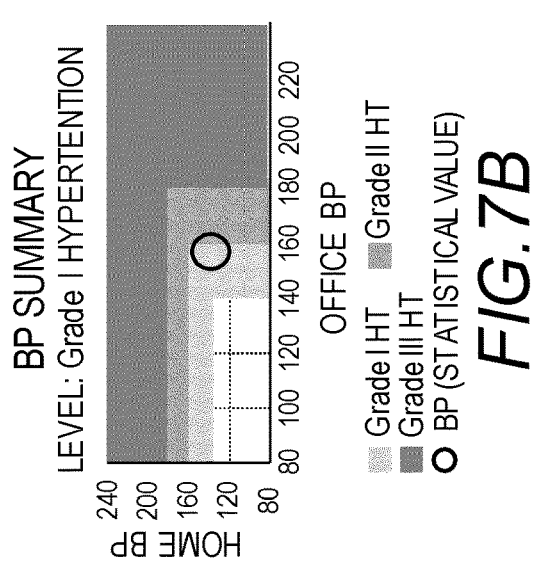
FIG.7F

RISK ANALYSIS SYSTEM AND RISK ANALYSIS METHOD

CROSS-REFERENCE TO RELATED APPLICATIONS

This application is a Continuation of International Patent Application No. PCT/JP2017/023511, filed Jun. 27, 2017, which claims the benefit of Japanese Patent Application No. 2016-134248, filed Jul. 6, 2016. These applications are incorporated by reference herein in their entirety.

BACKGROUND OF THE INVENTION

Technical Field

The present invention relates to a technique for analyzing a risk related to the health of a subject.

Background Art

Even for a healthy person, a risk of developing a disease is not nonexistent. In order to maintain a healthy and safe lifestyle, it is important to accurately assess one's own health risks and factors thereof, take appropriate measures including improvement of lifestyle habits and necessary treatment, and furthermore, subscribe to health insurance and save for the future. Considering health insurance policies and savings plans should involve roughly estimating medical expenses to be incurred in the future (hereinafter, referred to as "future medical expenses") to ensure that one's saving is neither excessive nor deficient. However, predicting future medical expenses can be challenging to a lay-person. In addition, although average future medical expenses may be determined by consulting an expert such as a financial planner, since average future medical expenses do not take health conditions and health risks of an individual into consideration, there is a lack in accuracy.

On the other hand, insurers who provide health insurance also have a strong need for predicting, as accurately as possible, health risks and future medical expenses of an insurance subscription applicant. Insurers incorporate such information into underwriting health insurance and designing terms and conditions (an insurance plan, a coverage amount, add-on options, and the like). However, as it stands, there is no mechanism capable of taking health conditions and health risks of an individual into consideration to predict future medical expenses of the individual with high reliability.

As an example of related prior art, PTL 1 discloses a system which automatically evaluates a propriety of underwriting or terms and conditions of life insurance in response to input of age and gender of an insurance subscription applicant, contents of a life insurance policy (an amount of death protection, a type of insurance, types of add-on options, and the like), and results of a physical checkup (blood pressure, BMI, uric acid level, and the like). PTL 2 discloses a system which collects measured data of blood pressure of an insured person through a network and changes, in accordance with the number of days on which blood pressure readings were taken during past three months and a proportion of readings in which the blood pressure fell within a prescribed value, a coverage amount (such as a hospitalization benefit) with respect to the insured person. PTL 3 discloses a system which analyzes, from information on statements of medical expenses accumulated in a certain period of time, medical expenses for each injury or disease and an increase in such medical expenses when a plurality of injuries and diseases occur concurrently and which uses a result of the analysis to find an insured person of which medical expenses have increased suddenly and to provide health guidance to the insured person. However, none of the literature discloses prediction of future medical expenses.

CITATION LIST

Patent Literature

PTL 1: Japanese Patent Application Laid-open No. 2003-31127

PTL 2: Japanese Patent Application Laid-open No. 2016-4430

PTL 3: Japanese Patent Application Laid-open No. 2011-39653

SUMMARY OF INVENTION

The present invention has been made in consideration of the circumstances described above and an object thereof is to provide a technique for predicting an amount of medical expenses to be incurred in the future with high reliability.

A risk analysis system according to the present invention includes: a storage apparatus which stores subject data including information related to health of a subject; an analyzer which analyzes a risk related to the health of the subject based on the subject data acquired from the storage apparatus; and an output apparatus which outputs a result of an analysis by the analyzer, wherein the analyzer includes: a risk estimating unit which estimates an event onset risk of the subject based on the subject data; and a medical expense predicting unit which predicts future medical expenses to be incurred in the future by the subject based on the event onset risk estimated by the risk estimating unit and the subject data.

According to this configuration, an event onset risk of a subject is first estimated and future medical expenses of the subject are predicted based on the event onset risk. Therefore, highly reliable future medical expenses which take health conditions and health risks of the subject into consideration can be predicted. In this case, an "event" refers to a phenomenon which adversely affects health and is typically a "disease". The term "event onset" may be replaced with "disease onset".

The risk estimating unit may estimate, as the event onset risk, an onset probability at which the subject develops a disease, and the medical expense predicting unit may calculate, based on the subject data, medical expenses needed when the subject develops the disease, and may predict, based on the medical expenses and the onset probability, future medical expenses of the subject.

According to this configuration, future medical expenses can be predicted with high reliability using a relatively simple algorithm. Specifically, since "medical expenses needed when a disease develops" is not dependent on an individual, an average amount of medical expenses can be easily obtained from, for example, previous data on statements of medical expenses, statistical data compiled by the Ministry of Health, Labour and Welfare, and the like. In addition, by combining the average medical expenses with the "onset probability at which a subject develops a disease" which is individual-dependent, future medical expenses which takes health conditions and health risks of the subject into consideration can be calculated.

The medical expense predicting unit may calculate, as the medical expenses needed when the subject develops the disease, hospitalization medical expenses required for hospitalization and outpatient medical expenses required for outpatient care. For example, a sum of the hospitalization medical expenses and the outpatient medical expenses may be adopted as the medical expenses of the subject. According to this configuration, since both hospitalization medical expenses and outpatient medical expenses are calculated, more realistic medical expenses can be predicted.

The risk estimating unit may estimate the onset probability for each of a plurality of diseases, and the medical expense predicting unit may predict the future medical expenses for each of the plurality of diseases and calculate total future medical expenses of the subject by adding up the predicted future medical expenses. Diseases that a subject may potentially develop are not limited to just one disease. For example, it is possible that a same subject may develop a plurality of diseases such as a cerebrovascular disease and a coronary artery disease. Therefore, according to this configuration, by estimating an onset probability for each of a plurality of diseases, more realistic medical expenses can be predicted.

An insurance subscription propriety determining unit may be provided which, by estimating an insurance premium amount to be paid when the subject subscribes to health insurance and comparing the predicted future medical expenses with the estimated insurance premium amount, determines a propriety of subscription to the health insurance by the subject. In addition, the output apparatus may output conditions and/or an insurance premium amount of health insurance suitable for the subject based on a determination result from the insurance subscription propriety determining unit. According to this configuration, a propriety of subscription to health insurance can be readily determined with high reliability. The result of the propriety determination may be used as reference information when a subject considers subscription to health insurance or may be used as reference information when an insurer who provides health insurance evaluates underwriting or designs terms and conditions for a subject (an insurance subscription applicant).

The output apparatus may generate and output a graph indicating an annual trend of the future medical expenses of the subject. Since an event onset risk changes over time (normally, the risk increases with the passage of time), future medical expenses also change over time. Outputting the graph described above enables a change in future medical expenses over time to be readily confirmed. For example, the graph may be used by a subject as reference for a financial plan when considering subscription to health insurance or formulating a savings plan or may be used as reference information when an insurer who provides health insurance evaluates underwriting or designs terms and conditions for a subject (an insurance subscription applicant).

The analyzer may include a plurality of types of analysis algorithms for different races and/or different areas of residence, and may select an analysis algorithm in accordance with a race and/or area of residence of the subject. Different races carry different event onset risks due to differences in genetics. In addition, even within the same race, a difference in areas of residence results in a difference in event onset risks due to differences in lifestyle habits. Furthermore, different areas of residence have different healthcare systems and commodity prices, which result in different medical expenses. Therefore, by adopting a configuration in which a suitable analysis algorithm is selected in accordance with the race and/or the area of residence as described above, an event onset risk can be estimated and future medical expenses can be predicted with high accuracy.

The analyzer may further include a hypertension determining unit which determines hypertension of the subject based on the subject data, and the risk estimating unit may estimate the event onset risk of the subject using a determination result from the hypertension determining unit as a risk factor. Hypertension is known to elevate an onset risk of vascular events. Therefore, by considering hypertension as a risk factor when estimating an event onset risk, reliability of risk estimation can be increased.

When it is determined by the hypertension determining unit that the subject has hypertension, the medical expense predicting unit may predict the future medical expenses of the subject by also taking medical expenses needed to treat hypertension into consideration. For example, hypertension often requires continuous treatment including hospital visits and medication. Therefore, by also taking medical expenses needed to treat hypertension into consideration, accuracy of prediction of future medical expenses can be further increased.

The present invention can be considered a risk analysis system including at least a part of the components or functions described above. In addition, the present invention can also be considered a risk analysis method which includes at least a part of the processes described above. Furthermore, the present invention can also be considered a program for executing each step of a risk analysis method which includes at least a part of the processes described above or a computer-readable recording medium which records such a program on a non-transitory basis. Moreover, the present invention can also be considered a display apparatus or a terminal which displays an analysis result output by the risk analysis system or the risk analysis method described above. The respective components and processes described above can be combined with one another in any way possible to constitute the present invention insofar as technical contradictions do not arise.

According to the present invention, an amount of medical expenses to be incurred in the future can be predicted with high reliability.

BRIEF DESCRIPTION OF THE DRAWINGS

FIGS. 5A to 5C each represent a display example of a result of insurance subscription propriety determination;

FIG. 6 represents an example of a screen for displaying a list of risk analysis information of a plurality of subjects;

FIGS. 7A to 7F each represent an example of a detailed display of risk analysis information of an individual subject.

DESCRIPTION OF THE EMBODIMENTS

Hereinafter, preferred embodiments of the present invention will be described with reference to the drawings.

However, it is to be understood that the description of the respective components presented below are intended to be changed as deemed appropriate in accordance with configurations of apparatuses and various conditions of apparatuses to which the present invention is to be applied and are not intended to limit the scope of the invention to the description presented below.

Figure 1:
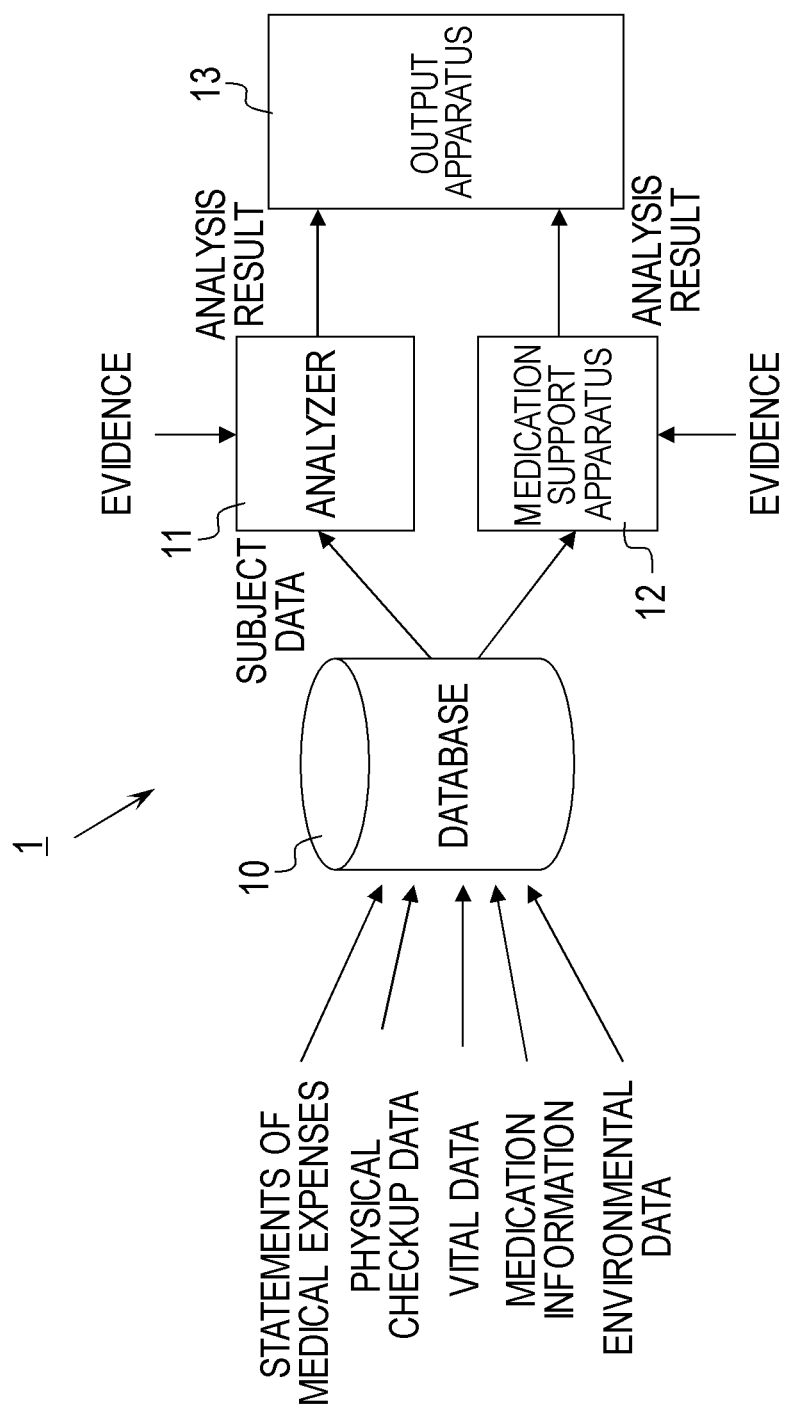
FIG. 1 is a diagram showing an overall configuration of a risk analysis system according to an embodiment of the present invention.

FIG. 1 schematically shows an overall configuration of a risk analysis system according to an embodiment of the present invention.

A risk analysis system 1 is a system which, based on information related to the health of a subject (hereinafter, referred to as "subject data"), analyzes health risks (a hypertension risk, an event onset risk, and the like) of the subject and generates output in accordance with a purpose based on an analysis result. The risk analysis system 1 according to the present embodiment is generally configured to include a database 10, an analyzer 11, a medication support apparatus 12, and an output apparatus 13.

The database 10 is a large-capacity storage apparatus which collects and manages subject data. For example, subject data may include data on statements of medical expenses, physical checkup data, vital data such as blood pressure, medication information, and environmental data (information related to surrounding environment which may affect an event onset risk such as structure of residence, climate in area of residence or place of work, and family makeup).

The analyzer 11 is a functional unit which analyzes health risks of a subject based on subject data. In addition, the medication support apparatus 12 is a functional unit which determines a medication method suitable for a pathological condition of the subject based on subject data and a result of risk analysis. The analyzer 11 and the medication support apparatus 12 preferably perform risk analysis and determine a medication method based on evidence (for example, guidelines provided by the academic community, papers, and opinions of KOLs (Key Opinion Leaders)). Furthermore, the output apparatus 13 is a functional unit which generates a report based on an analysis result of the analyzer 11 or a processing result of the medication support apparatus 12 and provides the subject or a user of the system 1 with the report. Information provided by the output apparatus 13 is displayed on, for example, a display apparatus of a terminal of the subject or a display apparatus included in the system 1. As the terminal of the subject, for example, a personal computer, a smartphone, a tablet terminal, or a mobile phone can be used.

For example, the system 1 can be used by an individual subject for the purposes of health management and self-check of risks or used by a physician, a nurse, a public health nurse, or the like for the purposes of analyzing a health condition of a patient and creating a treatment policy or guidance contents. In addition, the present system 1 can also be preferably applied to an insurance company for the purposes of subjectively analyzing health conditions and health risks of a client (an insurance subscription applicant) and using the analysis result to propose an insurance policy suitable for the client, determine a propriety of insurance subscription, set terms and conditions, and the like.

The risk analysis system 1 can be constituted by a general-purpose computer equipped with a CPU (a processor), a memory, a large-capacity storage, an input apparatus (a keyboard, a mouse, a touch panel, or the like), a display apparatus, a communication I/F, and the like. In this case, the risk analysis system 1 may be constituted by a single computer or the risk analysis system 1 may be realized by a plurality of computers cooperating with one another. For example, constructing a robust and convenient system using techniques related to decentralized computing or cloud computing is also desirable. When configuring the system using a plurality of computers, the computers may be installed at one location or installed in a distributed manner at a plurality of locations (which may be in different countries). Each function of the risk analysis system 1 according to the present embodiment is realized when a necessary program is executed by the CPU. However, a part of or all of the functions can also be constituted by a circuit such as an ASIC or an FPGA.

(Analyzer)

Figure 2:
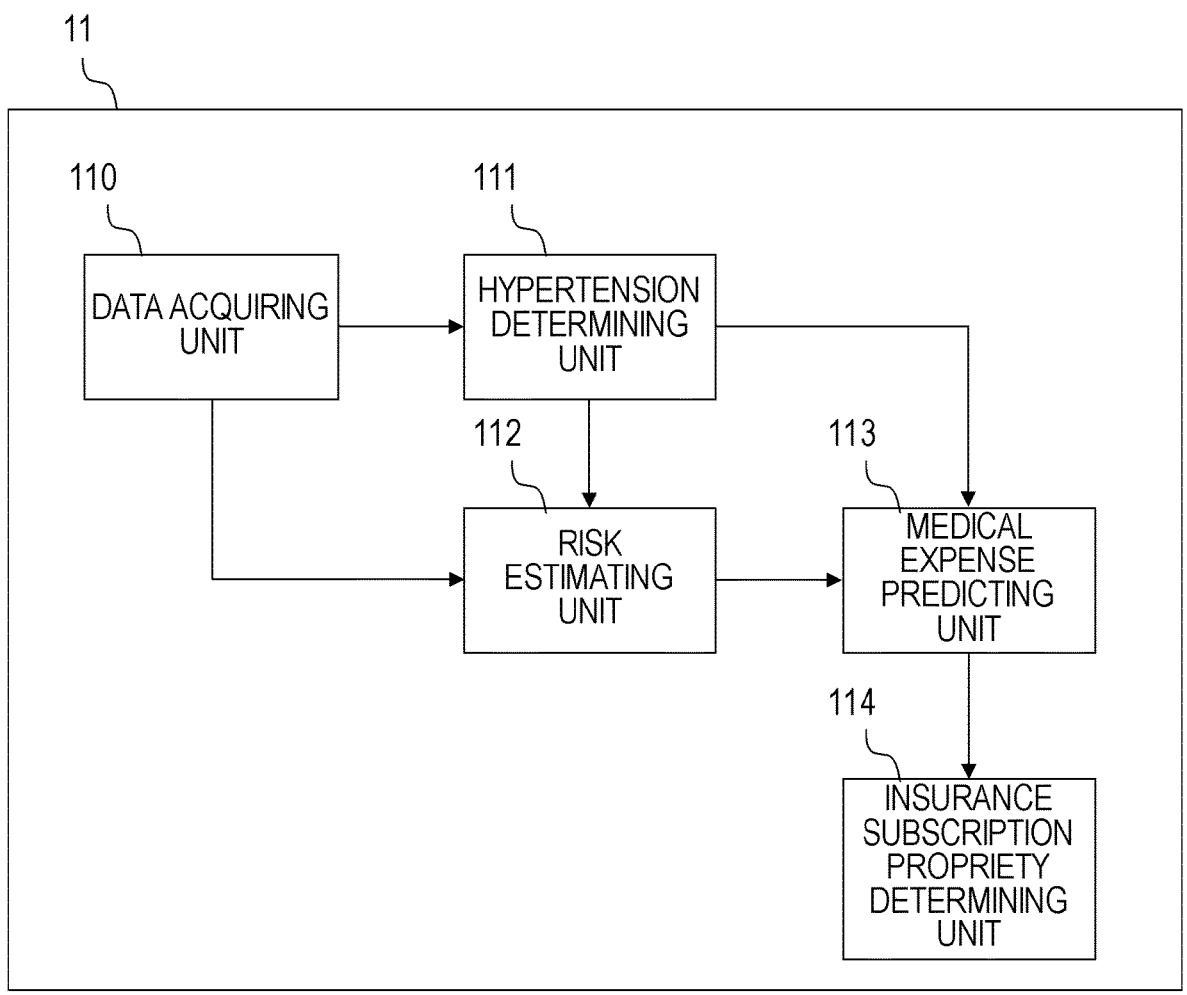
FIG. 2 is a block diagram showing a functional configuration of an analyzer.

FIG. 2 is a block diagram showing a functional configuration of the analyzer 11. The analyzer 11 includes, as functions thereof, a data acquiring unit 110, a hypertension determining unit 111, a risk estimating unit 112, a medical expense predicting unit 113, and an insurance subscription propriety determining unit 114. The data acquiring unit 110 is a function for acquiring necessary subject data from the database 10, and the hypertension determining unit 111 is a function for determining hypertension based on the subject data. The risk estimating unit 112 is a function for estimating an onset risk of a cerebrovascular event or a coronary artery event based on a result of the hypertension determining unit 111 and subject data. The medical expense predicting unit 113 is a function for predicting medical expenses to be incurred in the future by the subject (referred to as "future medical expenses") based on a result of the hypertension determining unit 111 and a result of the risk estimating unit 112. The insurance subscription propriety determining unit 114 is a function for determining a propriety of subscription to health insurance by the subject by comparing the predicted future medical expenses with an insurance premium amount.

Hereinafter, a specific example of processing by the analyzer 11 will be described.

(1) Acquisition of Subject Data

The data acquiring unit 110 acquires subject data necessary for risk analysis from the database 10. In the present embodiment, at least blood pressure data and physical checkup data of the subject are used as subject data.

As blood pressure data, desirably, both office blood pressure measured at a hospital or the like and home blood pressure measured at home or the like are acquired. In addition, as home blood pressure, three types of data including morning blood pressure, evening blood pressure, and night-time blood pressure are favorably acquired. Morning blood pressure refers to blood pressure measured within one hour after awakening and micturition and before taking breakfast, and evening blood pressure refers to blood pressure measured before bedtime. Night-time blood pressure refers to blood pressure measured while asleep. One to two weeks' worth of data is favorably used for morning and evening blood pressure, and one to two days' worth of data (with three to four readings taken per day) is favorably used for night-time blood pressure.

For example, in addition to basic data of the subject including age, gender, height, and weight, physical checkup data favorably includes inspection data such as a body-mass index (BMI), HDL cholesterol, LDL cholesterol, an estimated glomerular filtration rate (eGFR), fasting blood glucose, and HbA1c as well as reference data such as pre-existing disorders, diseases currently being treated, medications currently being taken, and lifestyle habits (smoking habits, alcohol consumption, sleeping hours, and the like).

(2) Determination of Hypertension

The hypertension determining unit 111 determines hypertension of the subject based on blood pressure data of the subject. Specifically, the hypertension determining unit 111 determines whether a blood pressure reading taken from the subject indicates normal range blood pressure or hypertension and, in the case of hypertension, determines a level thereof. A determination procedure and determination criteria of hypertension are desirably in accordance with reliable evidence. The hypertension determining unit 111 according to the present embodiment determines a blood pressure level by a classification shown in Table 1 in accordance with "Guidelines for the Management of Hypertension 2014 (JSH 2014)" published by the Japanese Society of Hypertension. Although systolic blood pressure is used for determining a blood pressure level in the present embodiment, alternatively, diastolic blood pressure may be used or both systolic blood pressure and diastolic blood pressure may be used.

TABLE 1

| Systolic blood pressure conditions | Classification (Level) |
|---|---|
| BP < 140 mmHg | Normal range BP |
| BP = 140 mmHg~159 mmHg | Grade I Hypertension |
| BP = 160 mmHg~179 mmHg | Grade II Hypertension |
| BP ≥ 180 mmHg | Grade III Hypertension |

In addition, when subject data includes data of both office blood pressure and home blood pressure, the hypertension determining unit 111 can determine a hypertension type in accordance with criteria shown in Table 2.

TABLE 2

| Systolic blood pressure conditions | Type of Hypertension |
|---|---|
| Office BP ≥ 140 mmHg and Home BP ≥ 135 mmHg | Hypertension |
| Office BP < 140 mmHg and Home BP ≥ 135 mmHg | Masked Hypertension |
| Office BP ≥ 140 mmHg and Home BP < 135 mmHg | White-coat Hypertension |

White-coat hypertension refers to a state in which a blood pressure reading taken in a doctor's office exhibits hypertension but out-of-office blood pressure (such as home blood pressure) indicates normal range blood pressure. Conversely, masked hypertension refers to a state in which a blood pressure reading taken in a doctor's office exhibits normal range blood pressure but out-of-office blood pressure (such as home blood pressure) indicates hypertension. Since masked hypertension is manifested as three pathological conditions including early-morning hypertension, diurnal hypertension, and nocturnal hypertension, the hypertension determining unit 111 determines that a pathological condition is any of early-morning, diurnal, and nocturnal hypertension based on a time point at which the home blood pressure exceeds 135 mmHg.

Furthermore, the hypertension determining unit 111 is also capable of determining an abnormality in blood pressure based on a circadian variability of blood pressure. For example, non-dipper nocturnal hypertension or riser nocturnal hypertension can be detected based on a variability of nocturnal blood pressure. Non-dipper nocturnal hypertension refers to a state where blood pressure does not drop during night-time (a normal person experiences a night-time dip in blood pressure), and riser nocturnal hypertension refers to a state where blood pressure rises during night-time.

(3) Estimation of Risk

The risk estimating unit 112 estimates an onset risk of a cerebrovascular event or a coronary artery event based on subject data. In doing so, the risk estimating unit 112 may consider a determination result from the hypertension determining unit 111 as a risk factor. This is because hypertension is a factor of increasing the onset probability of a cerebrovascular event or a coronary artery event.

A risk estimation process by the risk estimating unit 112 is desirably performed in accordance with reliable evidence. In the present embodiment, for example, the "Suita Score" developed by the National Cerebral and Cardiovascular Center, the "Multipurpose Cohort Study (JPHC Study)" by the National Cancer Center Japan, "NIPPON DATA 80/90", or the like is used.

The Suita Score is a risk score for predicting a 10-year onset risk of a coronary artery event (for example, ischemic heart diseases such as myocardial infarction and angina). A 10-year onset risk of a coronary artery event can be predicted by inputting, as risk factors, age, gender, smoking habits, presence of diabetes, hypertension level, LDL cholesterol, HDL cholesterol, and level of chronic kidney disease (CKD) (an eGFR value). In addition, a prediction model developed as an outcome of the JPHC Study can be used to predict a 10-year onset risk of a cerebrovascular event (for example, cerebral stroke or cerebral infarction) by inputting, as risk factors, age, gender, smoking habits, a body-mass index (BMI), presence of diabetes, hypertension level, and presence of oral administration of antihypertensive medication. Since these risk scores are well known, a detailed description will be omitted here.

(4) Prediction of Future Medical Expenses

Figure 3:
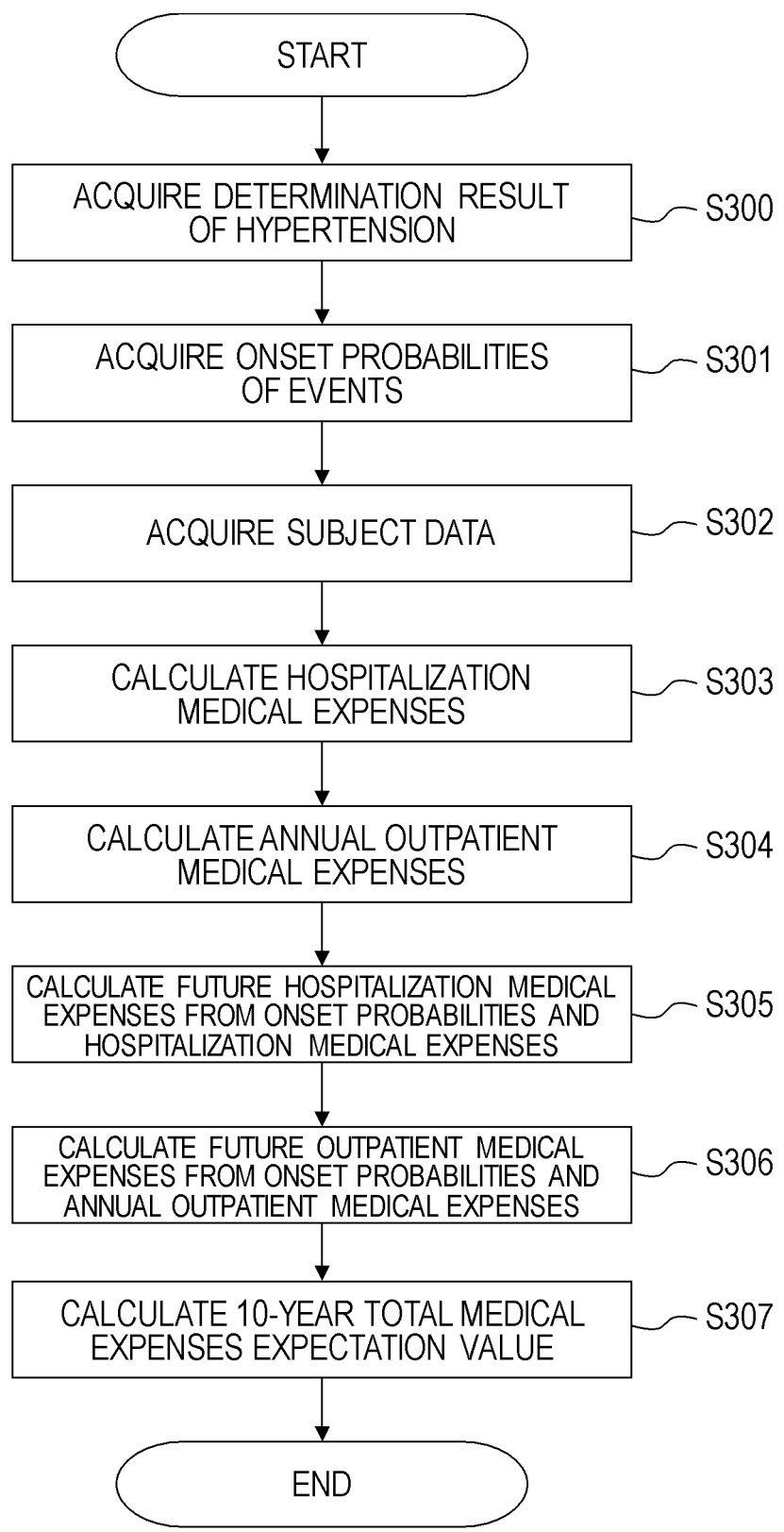
FIG. 3 is a flow chart showing a specific flow of a prediction process of future medical expenses.

A specific flow of a prediction process of future medical expenses by the medical expense predicting unit 113 according to the present embodiment will now be described based on the flow chart shown in FIG. 3.

First, the medical expense predicting unit 113 acquires a hypertension level (normal range/grade I hypertension/grade II hypertension/grade III hypertension) determined by the hypertension determining unit 111, respective onset probabilities of a coronary artery event and a cerebrovascular event estimated by the risk estimating unit 112, and subject data (steps S300 to S302). As subject data, at least information on the gender and the age of a subject is used.

The medical expense predicting unit 113 respectively calculates hospitalization medical expenses necessary when developing a coronary artery disease and hospitalization medical expenses necessary when developing a cerebrovascular disease (step S303). Hospitalization medical expenses refer to total medical expenses necessary for hospitalization when acquiring a disease and may be calculated by the following equation.

Hospitalization medical expenses=one-time medical expenses+one-day hospital stay medical expenses×length of stay The "one-time medical expenses" refer to medical expenses for medical actions that occur only once during a hospital stay. In the present embodiment, a sum of medical expenses for three medical actions including "first visit or revisit", "surgery", and "anesthesia" is adopted as the one-time medical expenses. The "one-day hospital stay medical expenses" refer to medical expenses necessary per day of hospital stay. In the present embodiment, a sum of medical expenses per day for eight medical actions including "clinical administration, etc.", "examination", "diagnostic imaging", "medication", "injection", "treatment", "rehabilitation", and "hospitalization charges, etc." is adopted as the one-day hospital stay medical expenses. As an amount of medical expenses for each medical action, an average amount is favorably obtained in advance based on statistical information. For example, in Statistics of Medical Care Activities in Public Health Insurance published by the Ministry of Health, Labour and Welfare, the number of cases, the actual number of days for care, and the number of cases, the number of times, points, and the total number of medical treatment by each medical action are compiled for each disease. Using such statistical information enables average medical expenses for each medical action to be calculated.

"Length of stay" is determined based on the gender and age of the subject and the type of disease. In the present embodiment, Table 3 (table for men) and Table 4 (table for women) are prepared in advance, and a length of stay corresponding to the gender and the age of the subject and the type of disease is acquired. Average values based on statistical information may be used as the values of the lengths of stay in the tables. For example, the following tables represent examples created based on the 2014 Patient Survey compiled by the Ministry of Health, Labour and Welfare.

TABLE 3

| Age | Coronary artery disease | Cerebrovascular disease |
|---|---|---|
| 20~24 | 6.4 | 21.4 |
| 25~29 | 6.5 | 23.2 |
| 30~34 | 4.4 | 33.6 |
| 35~39 | 5.8 | 52.5 |
| 40~44 | 6 | 38.1 |
| 45~49 | 5.9 | 37.6 |
| 50~54 | 5.8 | 68.5 |
| 55~59 | 5.4 | 47 |
| 60~64 | 5.8 | 52.9 |
| 65~69 | 5.7 | 64.1 |
| 70~74 | 5.7 | 59 |
| 75~79 | 7.6 | 70.9 |
| 80~84 | 9.3 | 77.6 |
| 85~89 | 12.9 | 97 |
| 90 and older | 12.7 | 132.3 |

TABLE 4

| Age | Coronary artery disease | Cerebrovascular disease |
|---|---|---|
| 20~24 | 2 | 23.8 |
| 25~29 | 3.3 | 62.9 |
| 30~34 | 8.4 | 21.1 |
| 35~39 | 6.1 | 43.2 |
| 40~44 | 4.9 | 30 |
| 45~49 | 6.4 | 26.5 |
| 50~54 | 5.2 | 30.9 |
| 55~59 | 4.6 | 37.6 |
| 60~64 | 4.8 | 48.9 |
| 65~69 | 10.4 | 70.3 |
| 70~74 | 5.8 | 76.3 |
| 75~79 | 6.9 | 88.6 |
| 80~84 | 11.2 | 101.6 |
| 85~89 | 21.6 | 153.1 |
| 90 and older | 57.7 | 214.6 |

In addition, the medical expense predicting unit 113 respectively calculates annual outpatient medical expenses necessary for treating a coronary artery disease, annual outpatient medical expenses necessary for treating a cerebrovascular disease, and annual outpatient medical expenses for treating hypertension (step S304). Annual outpatient medical expenses refer to total medical expenses necessary for hospital visits per year and may be calculated by the following equation.

Annual outpatient medical expenses=one-time outpatient medical expenses×number of hospital visits per year The "one-time outpatient medical expenses" refer to medical expenses necessary per one hospital visit. In the present embodiment, a sum of medical expenses per day for nine medical actions including "first visit or revisit", "clinical administration, etc.", "examination", "diagnostic imaging", "medication", "injection", "treatment", "rehabilitation", and "hospitalization charges, etc." is adopted as the one-time outpatient medical expenses. As an amount of medical expenses for each medical action, an average amount is favorably obtained in advance based on statistical information in a similar manner to hospitalization medical expenses. However, with respect to hypertensive diseases, in consideration of the fact that dosage differs in accordance with hypertension level, medical expenses for "medication" are multiplied by a coefficient in accordance with the hypertension level.

The "number of hospital visits per year" is determined based on the gender and the age of the subject and the type of disease. Table 5 is a table defining average medical care intervals per disease and per age for men, and FIG. 6 is a table defining average medical care intervals per disease and per age for women. Using average medical care intervals acquired from these tables, the number of hospital visits per year can be obtained by the following equation.

Number of hospital visits per year=365/average medical care intervals

An average value based on statistical information may be used as the value of the average medical care intervals. For example, the following tables represent examples created based on the 2014 Patient Survey compiled by the Ministry of Health, Labour and Welfare.

TABLE 5

| Age | Hypertensive disease | Coronary artery disease | Cerebrovascular disease |
|---|---|---|---|
| 20~24 | 20.1 | 30 | 9.7 |
| 25~29 | 17.6 | 15.2 | 14.8 |
| 30~34 | 16.3 | 11 | 9.5 |
| 35~39 | 18.3 | 14 | 12.1 |
| 40~44 | 19.8 | 16.4 | 9.6 |
| 45~49 | 20.6 | 15.4 | 9.3 |
| 50~54 | 21 | 16.7 | 12.7 |
| 55~59 | 21.3 | 16.5 | 14.1 |
| 60~64 | 20.8 | 17.7 | 13.4 |
| 65~69 | 20.5 | 18 | 14.1 |
| 70~74 | 19 | 15.8 | 13.9 |
| 75~79 | 18 | 16.2 | 14.2 |
| 80~84 | 16.7 | 15.4 | 14.1 |
| 85~89 | 15.6 | 15.8 | 13.3 |
| 90 and older | 15.1 | 14.5 | 11.7 |

TABLE 6

| Age | Hypertensive disease | Coronary artery disease | Cerebrovascular disease |
| --- | --- | --- | --- |
| 20~24 | 18.3 | 21 | 16.2 |
| 25~29 | 7.7 | 11.2 | 4 |
| 30~34 | 17.2 | 2.9 | 8.7 |
| 35~39 | 14.8 | 13.7 | 5.9 |
| 40~44 | 19 | 9.4 | 11.8 |
| 45~49 | 18.2 | 17.8 | 13.4 |
| 50~54 | 20.3 | 14.8 | 12.4 |
| 55~59 | 20 | 16.7 | 12.9 |
| 60~64 | 20.2 | 16 | 12.6 |
| 65~69 | 19.7 | 16.7 | 15 |
| 70~74 | 18 | 15.9 | 15.2 |
| 75~79 | 16.8 | 16.1 | 14.5 |
| 80~84 | 15.7 | 15.8 | 13.8 |
| 85~89 | 15.4 | 14.7 | 12 |
| 90 and older | 14.8 | 13.6 | 12.5 |

Next, based on the hospitalization medical expenses calculated in step S303 and the onset probability for each disease (step S305), the medical expense predicting unit 113 calculates future hospitalization medical expenses which are hospitalization medical expenses to be incurred in the future by the subject using the following equation.

> Future hospitalization medical expenses=onset probability of coronary artery disease×hospitalization medical expenses for coronary artery disease+onset probability of cerebrovascular disease×hospitalization medical expenses for cerebrovascular disease In addition, based on the annual outpatient medical expenses calculated in step S304 and the onset probability for each disease (step S306), the medical expense predicting unit 113 calculates future outpatient medical expenses which are outpatient medical expenses to be incurred in the future by the subject using the following equation.

> Future outpatient medical expenses=onset probability of coronary artery disease×annual outpatient medical expenses for coronary artery disease+onset probability of cerebrovascular disease×annual outpatient medical expenses for cerebrovascular disease+annual outpatient medical expenses for hypertensive disease Next, the medical expense predicting unit 113 calculates a 10-year total medical expenses expectation value (step S307). The 10-year total medical expenses expectation value is a value representing how much expenses are to be required when it is assumed that an onset of a disease will inevitably occur once during a 10-year period. Assuming that hospitalization accompanying the onset of the disease occurs only once, the 10-year total medical expenses expectation value is calculated by the following equation.

> 10-year total medical expenses expectation value=future hospitalization medical expenses+(future outpatient medical expenses×10)/2

According to the processes described above, future hospitalization medical expenses, future outpatient medical expenses, and a 10-year total medical expenses expectation value can be calculated.

(5) Propriety Determination of Insurance Subscription

Figure 4:
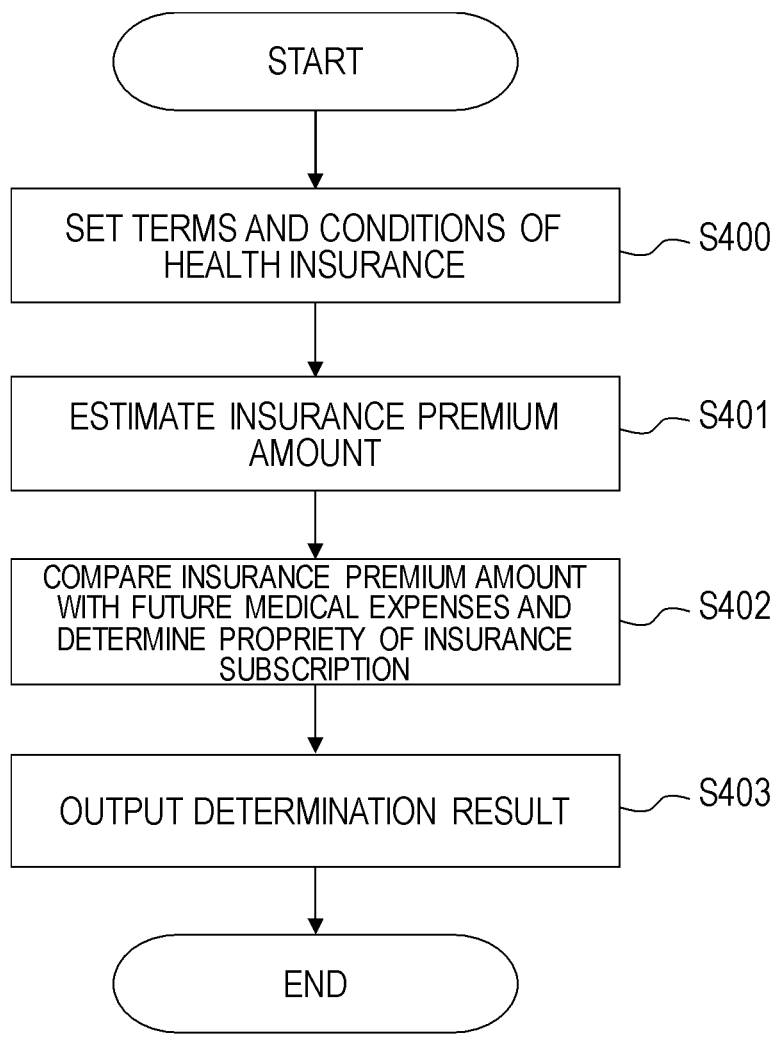
FIG. 4 is a flow chart showing a specific flow of an insurance subscription propriety determination process.

A specific flow of an insurance subscription propriety determination process by the insurance subscription propriety determining unit 114 according to the present embodiment will now be described based on the flow chart shown in FIG. 4.

First, the insurance subscription propriety determining unit 114 sets terms and conditions (an insurance plan, a coverage amount, add-on options, a policy duration, and the like) of health insurance to be considered (step S400). The terms and conditions may be input or selected by the subject or the insurance subscription propriety determining unit 114 may automatically set recommended conditions in accordance with the age, the gender, and preferences of the subject.

Next, based on the set terms and conditions and information such as the age and the gender of the subject, the insurance subscription propriety determining unit 114 estimates an insurance premium amount to be paid by the subject when subscribing to the health insurance (step S401). The insurance premium amount may be calculated on a single-year basis or an amount over the duration of the insurance policy may be calculated. In the present embodiment, it is assumed that a total insurance premium amount to be paid over 10 years is calculated for the purpose of comparing with future medical expenses.

Next, the insurance subscription propriety determining unit 114 determines a propriety of the subject subscribing to health insurance by comparing the insurance premium amount estimated in step S401 with the future medical expenses (for example, the 10-year total medical expenses expectation value) predicted by the medical expense predicting unit 113 (step S402), and outputs a determination result (step S403).

A logic of propriety determination differs depending on who uses the present system 1 for what kind of purpose. Specifically, when the subject (an insurance subscription applicant) uses the present system 1 for the purpose of considering health insurance that is suitable for the subject, since the benefit of the subject should be prioritized, a determination result of "subscription: appropriate" is favorably output when the insurance premium amount is smaller than the 10-year total medical expenses expectation value and a determination result of "subscription: inappropriate" is favorably output when the insurance premium amount is equal to or larger than the 10-year total medical expenses expectation value. FIG. 5A represents a display example of a determination result to be presented to an insurance subscription applicant.

On the other hand, when an insurer who provides health insurance uses the present system 1 for the purpose of underwriting a subject (an insurance subscription applicant), since the benefit of the insurer should be prioritized, a determination result of "subscription: appropriate" is favorably output when the insurance premium amount is larger than the 10-year total medical expenses expectation value and a determination result of "subscription: inappropriate" is favorably output when the insurance premium amount is equal to or smaller than the 10-year total medical expenses expectation value. FIG. 5B represents a display example of a determination result of a propriety of underwriting to be presented to an insurer.

The determination logic and display examples described herein are merely exemplary and other logic or criteria may be used. It is also preferable to output conditions and an insurance premium amount of health insurance suitable for the subject (the insurance subscription applicant) based on the determination result from the insurance subscription propriety determining unit 114. For example, optimal terms and conditions which provide a balance between the insurance premium amount and the 10-year total medical expenses expectation value may be selected from a plurality of terms and conditions and recommended to the subject (the insurance subscription applicant) or to the insurer. FIG. 5C represents an example of a recommendation output by the output apparatus 13. Alternatively, instead of a two-alternative choice between appropriate and inappropriate, a determination result may be output in a plurality of stages such as most appropriate, appropriate, and inappropriate. Performing such an output is advantageous for a person considering subscribing to insurance because the person can more readily select an insurance policy with suitable conditions and is also advantageous for an insurer because an increase in opportunities to subscribe to health insurance can be expected.

(Display Example of Risk Analysis Result)

A display example of a risk analysis result by the output apparatus 13 will be described.

FIG. 6 represents an example of a screen for displaying a list of risk analysis information of a plurality of subjects. Each row represents risk analysis information of one subject. In the example shown in FIG. 6, information related to a subject such as a user ID, an age, a gender, a trend in blood pressure, office blood pressure, home blood pressure, a vascular age, and a total risk is output as risk analysis information. As the trend in blood pressure, for example, a weekly variation (a graph) in systolic blood pressure or an average value, a maximum value, a minimum value, or the like of systolic blood pressure in a week may be displayed. The total risk is an index representing a comprehensive determination of onset risks of a cerebrovascular event and a coronary artery event and, in the example shown in FIG. 6, the total risk is indicated in four stages including "Low", "Middle", "High", and "Very High". In addition, an alert icon is displayed for subjects whose total risk is determined to be "Very High".

FIGS. 7A to 7F each represent an example of a detailed display of risk analysis information of an individual subject. FIG. 7A shows a display example of a stratification of blood pressure. An abscissa represents time of day (from 0 to 24 hours), and an ordinate represents blood pressure readings. Data plotted by triangles represent blood pressure (morning and evening blood pressure) readings taken during daytime and data plotted by squares represent blood pressure (nocturnal blood pressure) readings taken during nighttime. In the graph shown in FIG. 7A, respective blood pressure ranges of normal blood pressure, grade I hypertension, grade II hypertension, and grade III hypertension are depicted in different colors and, accordingly, in which blood pressure range a blood pressure reading of the subject is classified can be readily confirmed. In FIG. 7A, a systolic blood pressure range of 140 to 159 is adopted as grade I hypertension, a systolic blood pressure range of 160 to 179 is adopted as grade II hypertension, and a systolic blood pressure range of 180 and higher is adopted as grade III hypertension.

In addition, when white-coat hypertension, masked hypertension, an abnormal circadian variability of blood pressure (such as non-dipper nocturnal hypertension or riser nocturnal hypertension), and the like are detected in blood pressure data of the subject, such information may also be output.

FIG. 7B shows another display example of a stratification of blood pressure. An abscissa represents office blood pressure and an ordinate represents home blood pressure. The graph shown in FIG. 7B similarly depicts respective blood pressure ranges of normal blood pressure, grade I hypertension, grade II hypertension, and grade III hypertension in different colors. Data plotted by a circle indicates statistical values of blood pressure readings taken during a prescribed period of time. Specifically, a center of the circle represents an average value of blood pressure and a size (a diameter) of the circle represents a variation (a standard deviation, dispersibility, or the like) in blood pressure readings. Such a display enables in which blood pressure range a blood pressure reading of the subject is classified to be readily confirmed by looking at a position of the circle. In addition, when a classification according to office blood pressure (the abscissa) and a classification according to home blood pressure (the ordinate) are inconsistent, white-coat hypertension or masked hypertension is suspected. Furthermore, looking at the size of the circle enables whether blood pressure readings are stable or vary significantly to be intuitively assessed.

FIG. 7C represents a display example of a cerebrovascular risk. A comparison between the subject's score and an average score for the subject's age group is shown for each of five risk factors including blood pressure, body-mass index (BMI), smoking habits, diabetes, and blood pressure medication. In addition, FIG. 7D represents a display example of a coronary artery risk. A comparison between the subject's score and an average score for the subject's age group is shown for each of six risk factors including blood pressure, chronic kidney disease (an estimated glomerular filtration rate eGFR), smoking habits, diabetes, HDL cholesterol, and LDL cholesterol. By viewing the charts provided in FIGS. 7C and 7D, a presence or absence of a cerebrovascular risk and a coronary artery risk (whether or not there is a deviation from the average), items to be improved, and the like can be readily comprehended.

FIG. 7E represents a display example of respective onset risks of a cerebrovascular event and a coronary artery event. An ordinate represents a probability of developing an event within 10 years. By comparing and displaying an event onset risk of the subject and an average event onset risk for the subject's age group, how high or low the event onset risk of the subject is can be readily accessed. In addition, FIG. 7F represents a display example of a total risk which combines an onset risk of a cerebrovascular event and an onset risk of a coronary artery event. For example, a score obtained by weighting and adding up the onset risk of a cerebrovascular event and the onset risk of a coronary artery event and normalizing the sum within a range of 0 (minimum risk) to 100 (maximum risk) can be used as the total risk.

(Display Example of Future Medical Expenses)

Figures 8A, 8B:
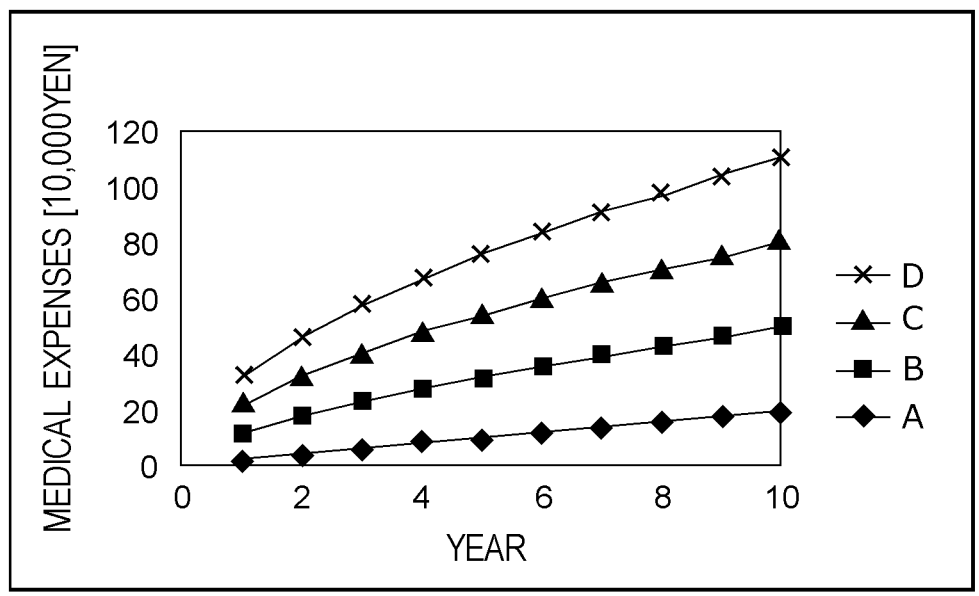
FIGS. 8A and 8B each represent a display example of future medical expenses.

FIGS. 8A and 8B each show a display example of future medical expenses by the output apparatus 13. FIG. 8A represents a screen example for presenting a 10-year total medical expenses expectation value predicted by the medical expense predicting unit 113 to the subject.

FIG. 8B represents a screen example which shows predicted values of annual future medical expenses as a graph. For example, estimation of medical expenses per year can be performed as follows.

When a 10-year onset probability of a given disease as estimated by the risk estimating unit 112 is denoted by p {p|0≤p≤1} and a year to be calculated is denoted by y {y|1≤y≤10}, a disease incidence P(y) in each year y can be calculated as follows. It should be noted that while a simple model for linearly predicting a disease onset probability is used in this case, a nonlinear model may be used instead.

$$P(y) = \frac{py}{10} \qquad \text{[Math. 1]}$$

When additional medical expenses to be incurred when developing a disease is denoted by Cp [yen] and basic annual medical expenses to be incurred independently of the disease is denoted by Cn [yen/year], average medical expenses µ(y) and a dispersion of medical expenses σ(y) in each year y are respectively calculated as follows.

$$\mu(y) = (Cp + Cn)P(y) + Cn\{1 - P(y)\} \quad \text{[Math. 2]}$$
$$\sigma(y) = \sqrt{\{(Cp + Cn - \mu(y)\}^2 P(y) + \{Cn - \mu(y)\}^2 \{1 - P(y)\}}$$

In this case, the additional medical expenses Cp is a sum of hospitalization medical expenses and outpatient medical expenses calculated by the medical expense predicting unit 113.

A graph A in FIG. 8B represents a trend in the average medical expenses µ(y) in a case where an onset probability p of a disease=0.1, additional medical expenses Cp=10,000,000 [yen], and basic annual medical expenses Cn=10,000 [yen/year]. In addition, graphs B, C, and D are graphs indicating a more pessimistic prediction than graph A, in which graphs B, C, and D respectively represent µ(y)+σ(y), µ(y)+2σ(y), and µ(y)+3σ(y). Viewing such graphs enable a prediction of medical expenses and a range of variation (a probability distribution) of predicted values for each year to be assessed. For example, the graph may be used by a subject as reference for a financial plan when considering subscription to health insurance or formulating a savings plan or may be used as reference information when an insurer who provides health insurance evaluates underwriting or designs terms and conditions for a subject (an insurance subscription applicant).

Advantages of the Present Embodiment

According to the configuration of the present embodiment described above, an event onset risk of a subject is first estimated and future medical expenses of the subject are predicted based on the event onset risk. Therefore, future medical expenses which take health conditions and health risks of the subject into consideration can be predicted. Furthermore, since risk estimation and medical expense prediction are performed based on reliable evidence and statistical data of public organizations (such as the Ministry of Health, Labour and Welfare), high reliability and accuracy are expected.

In addition, the present embodiment adopts an algorithm which predicts future medical expenses based on medical expenses needed when a disease develops and an onset probability of the disease. Since "medical expenses needed when a disease develops" is not dependent on an individual, an average amount of medical expenses can be easily obtained from, for example, previous data on statements of medical expenses, statistical data compiled by the Ministry of Health, Labour and Welfare, and the like. In addition, by combining the average medical expenses with the "onset probability" which is individual-dependent, future medical expenses which takes health conditions and health risks of the subject into consideration can be calculated.

In addition, in the present embodiment, since both hospitalization medical expenses and outpatient medical expenses are taken into consideration, more realistic medical expenses can be predicted. Furthermore, in the present embodiment, since risk estimation and prediction of future medical expenses are performed for two types of diseases, namely, a coronary artery event and a cerebrovascular event, the accuracy of predicting medical expenses can be increased. Moreover, in the present embodiment, since future medical expenses of a subject is predicted by also taking medical expenses needed to treat hypertension into consideration, the prediction accuracy of future medical expenses can be further increased.

In addition, since the present embodiment provides a function for automatically determining a propriety of insurance subscription based on future medical expenses and an insurance premium amount, an insurance subscription applicant or an insurer can readily determine the propriety of subscription to health insurance with high reliability.

Other Embodiments

The configuration of the embodiment described above merely represents a specific example of the present invention. The scope of the present invention is not limited to the embodiment described above and various modifications can be made without departing from the scope of technical concepts of the invention.

For example, while evidence based on results of research performed in Japan such as the Suita Score and the JPHC Study are used in the embodiment described above, when the subject of the present system 1 is non-Japanese or resides in a country other than Japan, evidence in accordance with the subject's race or area of residence is desirably used. This is because different races carry different event onset risks due to differences in genetics, and even within the same race, a difference in areas of residence results in a difference in event onset risks due to differences in lifestyle habits. Furthermore, since different areas of residence have different healthcare systems and commodity prices which result in different medical expenses, the algorithm for predicting medical expenses may also be changed for each area of residence of the subject.

Specifically, a plurality of types of analysis algorithms (programs, tables, or the like) for different races and/or different areas of residence may be provided in advance and the risk estimating unit 112 or the medical expense predicting unit 113 may select an analysis algorithm in accordance with a race and/or area of residence of the subject. Information regarding the race and the area of residence can be supplied as subject data. In this manner, providing a function for adaptively changing algorithms in accordance with the race and the area of residence of the subject is advantageous in operating the system in countries made up of people of various races such as the United States.

What is claimed is:
1. A risk analysis system, comprising:
   a storage apparatus which stores subject data including information related to health of a subject;
   an analyzer which analyzes a risk related to the health of the subject based on the subject data acquired from the storage apparatus;
   an output apparatus which outputs an analysis result by the analyzer; and
   a display, wherein
   the subject data includes blood pressure data of the subject for a plurality of times which are measured during a predetermined period of time,
   the analyzer includes:
      a hypertension determining unit which calculates a statistical value of blood pressure of the subject from the blood pressure data for the plurality of times to determine a level of hypertension of the subject based on the statistical value of blood pressure;

a risk estimating unit which estimates an event onset risk of the subject based on the subject data and the level of hypertension;

a medical expense predicting unit which predicts future medical expenses, which are medical expenses to be incurred in the future by the subject, based on the event onset risk estimated by the risk estimating unit and the subject data; and an insurance subscription propriety determining unit which, by estimating an insurance premium amount to be paid when the subject subscribes to health insurance and comparing the predicted future medical expenses with the estimated insurance premium amount, determines a propriety of subscription to the health insurance by the subject;

the medical expense predicting unit predicts the predicted future medical expenses according to the following equations (1) to (3):

$$P(y) = \frac{py}{10} \quad (1)$$

$$\mu(y) = (Cp + Cn)P(y) + Cn\{1 - P(y)\} \quad (2)$$

$$\sigma(y) = \sqrt{\{(Cp + Cn - \mu(y))\}^2 P(y) + \{Cn - \mu(y)\}^2 \{1 - P(y)\}}, \quad (3)$$

where a 10-year onset probability of a given disease as estimated by the risk estimating unit is p {p|0≤p≤1}, a year to be calculated is y {y|1≤y≤10}, a disease incidence in each year y is P(y), additional medical expenses incurred when developing a disease is Cp, basic annual medical expenses incurred independently of the disease is Cn, average medical expenses is μ(v), and a dispersion of medical expenses is σ(y), the analyzer determines at least one graph according to the predicted future medical expenses predicted by the medical expense predicting unit, the output apparatus outputs the at least one graph to the display, and the display displays the at least one graph.

2. The risk analysis system according to claim 1, wherein the insurance subscription propriety determining unit compares the predicted future medical expenses with the estimated insurance premium amount and determines that it is inappropriate for the subject to subscribe to the health insurance when the insurance premium amount is equal to or lower than the future medical expenses.

3. The risk analysis system according to claim 1, wherein when the subject data includes data of office blood pressure and data of home blood pressure, the hypertension determining unit determines, based on the data of the office blood pressure and the data of the home blood pressure, whether the subject has hypertension, masked hypertension, or white-coat hypertension.

4. The risk analysis system according to claim 3, wherein the hypertension types include hypertension levels, and when the blood pressure of the subject is determined to be hypertension, the medical expense predicting unit predicts the future medical expenses of the subject by also taking medical expenses needed to treat hypertension into consideration based on a hypertension level of the subject.

5. The risk analysis system according to claim 1, wherein the risk estimating unit estimates, as the event onset risk, an onset probability at which the subject develops a disease, and the medical expense predicting unit calculates, based on the subject data, medical expenses needed when the subject develops the disease, and predicts, based on the medical expenses and the onset probability, the future medical expenses of the subject.

6. The risk analysis system according to claim 5, wherein the medical expense predicting unit calculates, as the medical expenses needed when the subject develops the disease, hospitalization medical expenses required for hospitalization and outpatient medical expenses required for outpatient care.

7. The risk analysis system according to claim 5, wherein the risk estimating unit estimates the onset probability for each of a plurality of diseases, and the medical expense predicting unit predicts the future medical expenses for each of the plurality of diseases, and calculates total future medical expenses of the subject by adding up the predicted future medical expenses.

8. The risk analysis system according to claim 1, wherein the output apparatus outputs conditions and/or an insurance premium amount of health insurance suitable for the subject based on a determination result from the insurance subscription propriety determining unit.

9. The risk analysis system according to claim 1, wherein the output apparatus generates and outputs a graph indicating an annual trend of the future medical expenses of the subject.

10. The risk analysis system according to claim 1, wherein the analyzer includes a plurality of types of analysis algorithms for different races and/or different areas of residence and selects an analysis algorithm in accordance with a race and/or area of residence of the subject.

11. The risk analysis system according to claim 1, wherein, when it is determined by the hypertension determining unit that the subject has hypertension, the medical expense predicting unit predicts the future medical expenses of the subject by also taking medical expenses needed to treat hypertension into consideration.

12. A risk analysis system, comprising:

a storage apparatus which stores subject data including information related to health of a subject;

an analyzer which analyzes a risk related to the health of the subject based on the subject data acquired from the storage apparatus; and an output apparatus which outputs an analysis result by the analyzer; and a display, wherein the subject data includes blood pressure data of the subject for a plurality of times which are measured during a predetermined period of time, the analyzer includes:

a hypertension determining unit which calculates a statistical value of blood pressure of the subject from the blood pressure data for the plurality of times to determine a level of hypertension of the subject based on the statistical value of blood pressure;

a risk estimating unit which estimates an event onset risk of the subject based on the subject data and the level of hypertension; and a medical expense predicting unit which predicts future medical expenses, which are medical expenses to be incurred in the future by the subject, based on the event onset risk estimated by the risk estimating unit and the subject data, and the analyzer includes a plurality of types of analysis algorithms for different areas of residence and selects an analysis algorithm in accordance with an area of residence of the subject;

the medical expense predicting unit predicts the predicted future medical expenses according to the following equations (1) to (3):

$$P(y) = \frac{py}{10} \quad (1)$$

$$\mu(y) = (Cp + Cn)P(y) + Cn\{1 - P(y)\} \quad (2)$$

$$\sigma(y) = \sqrt{\{(Cp + Cn - \mu(y))^2 P(y) + \{Cn - \mu(y)\}^2 \{1 - P(y)\}}, \quad (3)$$

where a 10-year onset probability of a given disease as estimated by the risk estimating unit is p $\{p|0 \le p \le 1\}$, a year to be calculated is y $\{y|1 \le y \le 10\}$, a disease incidence in each year y is P(y), additional medical expenses incurred when developing a disease is Cp, basic annual medical expenses incurred independently of the disease is Cn, average medical expenses is $\mu(v)$, and a dispersion of medical expenses is $\sigma(y)$, the analyzer determines at least one graph according to the predicted future medical expenses predicted by the medical expense predicting unit, the output apparatus outputs the at least one graph to the display, and the display displays the at least one graph.

13. The risk analysis system according to claim 12, further comprising an insurance subscription propriety determining unit which, by estimating an insurance premium amount to be paid when the subject subscribes to health insurance and comparing the predicted future medical expenses with the estimated insurance premium amount, determines a propriety of subscription to the health insurance by the subject.

14. A risk analysis method, comprising:
an acquiring step of acquiring subject data including information related to health of a subject;
an analyzing step of analyzing a risk related to the health of the subject based on the subject data; and
an outputting step of outputting an analysis result of the analyzing step, wherein
the subject data includes blood pressure data of the subject for a plurality of times which are measured during a predetermined period of time,
the analyzing step includes:
a hypertension determining step of calculating a statistical value of blood pressure of the subject from the blood pressure data for the plurality of times to determine a level of hypertension of the subject based on the statistical value of blood pressure;
a step of estimating an event onset risk of the subject based on the subject data and the level of hypertension;
a step of predicting future medical expenses, which are medical expenses to be incurred in the future by the subject, based on the estimated event onset risk and the subject data; and
a step of determining, by estimating an insurance premium amount to be paid when the subject subscribes to health insurance and comparing the predicted future medical expenses with the estimated insurance premium amount, a propriety of subscription to the health insurance by the subject;

in the step of predicting future medical expenses, the predicted future medical expenses are predicted according to the following equations (1) to (3):

$$P(y) = \frac{py}{10} \quad (1)$$

$$\mu(y) = (Cp + Cn)P(y) + Cn\{1 - P(y)\} \quad (2)$$

$$\sigma(y) = \sqrt{\{(Cp + Cn - \mu(y))^2 P(y) + \{Cn - \mu(y)\}^2 \{1 - P(y)\}}, \quad (3)$$

where a 10-year onset probability of a given disease as estimated in the step of estimating the event onset risk p $\{p|0 \le p \le 1\}$, a year to be calculated is y $\{y|1 \le y \le 10\}$, a disease incidence in each year y is P(y), additional medical expenses incurred when developing a disease is Cp, basic annual medical expenses incurred independently of the disease is Cn, average medical expenses is $\mu(y)$, and a dispersion of medical expenses is $\sigma(y)$, the analyzing step includes determining at least one graph according to the predicted future medical expenses predicted by the medical expense predicting unit, the outputting step includes outputting the at least one graph to a display, and the display displays the at least one graph.

15. The risk analysis method according to claim 14, wherein, in the step of determining a propriety of subscription to the health insurance by the subject, the predicted future medical expenses are compared with the estimated insurance premium amount and a determination that it is inappropriate for the subject to subscribe to the health insurance is made when the insurance premium amount is equal to or lower than the future medical expenses.

16. The risk analysis method according to claim 14, wherein
when the subject data includes data of office blood pressure and data of home blood pressure, whether the subject has hypertension, masked hypertension, or white-coat hypertension is determined based on the data of the office blood pressure and the data of the home blood pressure in the step of determining which of the hypertension types the blood pressure of the subject corresponds to.

17. A risk analysis method, comprising:
an acquiring step of acquiring subject data including information related to health of a subject;
an analyzing step of analyzing a risk related to the health of the subject based on the subject data; and
an outputting step of outputting an analysis result of the analyzing step, wherein
the subject data includes blood pressure data of the subject for a plurality of times which are measured during a predetermined period of time,
the analyzing step includes:
a hypertension determining step of calculating a statistical value of blood pressure of the subject from the blood pressure data for the plurality of times to determine a level of hypertension of the subject based on the statistical value of blood pressure;
a step of estimating an event onset risk of the subject based on the subject data the level of hypertension; and a step of predicting future medical expenses, which are medical expenses to be incurred in the future by the subject, based on the estimated event onset risk and the subject data, and in the analyzing step, an analysis algorithm in accordance with an area of residence of the subject is selected from a plurality of analysis algorithms prepared for different areas of residence;

in the step of predicting future medical expenses, the predicted future medical expenses are predicted according to the following equations (1) to (3):

$$P(y) = \frac{py}{10} \quad (1)$$

$$\mu(y) = (Cp + Cn)P(y) + Cn\{1 - P(y)\} \quad (2)$$

$$\sigma(y) = \sqrt{\{(Cp + Cn - \mu(y)\}^2 P(y) + \{Cn - \mu(y)\}^2 \{1 - P(y)\}}, \quad (3)$$

where a 10-year onset probability of a given disease as estimated in the step of estimating the event onset risk p {p|0≤p≤1}, a year to be calculated is y {y|1≤y≤10}, a disease incidence in each year y is P(y), additional medical expenses incurred when developing a disease is Cp, basic annual medical expenses incurred independently of the disease is Cn, average medical expenses is μ(y), and a dispersion of medical expenses is σ(y), the analyzing step includes determining at least one graph according to the predicted future medical expenses predicted by the medical expense predicting unit, the outputting step includes outputting the at least one graph to a display, and the display displays the at least one graph.

18. A non-transitory computer readable medium that stores a program causing a computer to execute a risk analysis method, the risk analysis method comprising:

an acquiring step of acquiring subject data including information related to health of a subject;

an analyzing step of analyzing a risk related to the health of the subject based on the subject data; and an outputting step of outputting an analysis result of the analyzing step, wherein the subject data includes blood pressure data of the subject for a plurality of times which are measured during a predetermined period of time, the analyzing step includes:

a hypertension determining step of calculating a statistical value of blood pressure of the subject from the blood pressure data for the plurality of times to determine a level of hypertension of the subject based on the statistical value of blood pressure;

a step of estimating an event onset risk of the subject based on the subject data and the level of hypertension;

a step of predicting future medical expenses, which are medical expenses to be incurred in the future by the subject, based on the estimated event onset risk and the subject data; and a step of determining, by estimating an insurance premium amount to be paid when the subject subscribes to health insurance and comparing the predicted future medical expenses with the estimated insurance premium amount, a propriety of subscription to the health insurance by the subject;

in the step of predicting future medical expenses, the predicted future medical expenses are predicted according to the following equations (1) to (3):

$$P(y) = \frac{py}{10} \quad (1)$$

$$\mu(y) = (Cp + Cn)P(y) + Cn\{1 - P(y)\} \quad (2)$$

$$\sigma(y) = \sqrt{\{(Cp + Cn - \mu(y)\}^2 P(y) + \{Cn - \mu(y)\}^2 \{1 - P(y)\}}, \quad (3)$$

where a 10-year onset probability of a given disease as estimated in the step of estimating the event onset risk p {p|0≤p≤1}, a year to be calculated is y {y|1≤y≤10}, a disease incidence in each year y is P(y), additional medical expenses incurred when developing a disease is Cp, basic annual medical expenses incurred independently of the disease is Cn, average medical expenses is μ(y), and a dispersion of medical expenses is σ(y), the analyzing step includes determining at least one graph according to the predicted future medical expenses predicted by the medical expense predicting unit, the outputting step includes outputting the at least one graph to a display, and the display displays the at least one graph.

19. A display apparatus which displays the analysis result output by a risk analysis method, the risk analysis method comprising:

an acquiring step of acquiring subject data including information related to health of a subject;

an analyzing step of analyzing a risk related to the health of the subject based on the subject data; and an outputting step of outputting an analysis result of the analyzing step, wherein the subject data includes blood pressure data of the subject for a plurality of times which are measured during a predetermined period of time, the analyzing step includes:

a hypertension determining step of calculating a statistical value of blood pressure of the subject from the blood pressure data for the plurality of times to determine a level of hypertension of the subject based on the statistical value of blood pressure;

a step of estimating an event onset risk of the subject based on the subject data and the level of hypertension;

a step of predicting future medical expenses, which are medical expenses to be incurred in the future by the subject, based on the estimated event onset risk and the subject data; and a step of determining, by estimating an insurance premium amount to be paid when the subject subscribes to health insurance and comparing the predicted future medical expenses with the estimated insurance premium amount, a propriety of subscription to the health insurance by the subject;

in the step of predicting future medical expenses, the predicted future medical expenses are predicted according to the following equations (1) to (3):

$$P(y) = \frac{py}{10} \quad (1)$$

-continued $$\mu(y) = (Cp + Cn)P(y) + Cn\{1 - P(y)\} \quad (2)$$

$$\sigma(y) = \sqrt{\{(Cp + Cn - \mu(y))\}^2 P(y) + \{Cn - \mu(y)\}^2 \{1 - P(y)\}}, \quad (3)$$

where a 10-year onset probability of a given disease as estimated in the step of estimating the event onset risk p $\{p|0 \leq p \leq 1\}$, a year to be calculated is y $\{y|1 \leq y \leq 10\}$, a disease incidence in each year y is $P(y)$, additional medical expenses incurred when developing a disease is Cp, basic annual medical expenses incurred independently of the disease is Cn, average medical expenses is $\mu(y)$, and a dispersion of medical expenses is $\sigma(y)$, the analyzing step includes determining at least one graph according to the predicted future medical expenses predicted by the medical expense predicting unit, the outputting step includes outputting the at least one graph to a display, and the display displays the at least one graph.

* * * * *